United States Patent
Hincapie Ordonez et al.

(10) Patent No.: US 10,555,726 B2
(45) Date of Patent: Feb. 11, 2020

(54) PERCUTANEOUS TOOLS FOR MINIMALLY INVASIVE ACCESS TO THE CAROTID SHEATH FOR VAGUS NERVE STIMULATION

(71) Applicant: Cardiac Pacemakers, Inc., St. Paul, MN (US)

(72) Inventors: Juan Gabriel Hincapie Ordonez, Maple Grove, MN (US); Bruce A. Tockman, Scandia, MN (US); Brian Soltis, St. Paul, MN (US); Lili Liu, Maple Grove, MN (US); Eric F. Hammill, Ham Lake, MN (US)

(73) Assignee: Cardiac Pacemakers, Inc, St Paul, MN (US)

( * ) Notice: Subject to any disclaimer, the term of this patent is extended or adjusted under 35 U.S.C. 154(b) by 971 days.

(21) Appl. No.: 14/743,803

(22) Filed: Jun. 18, 2015

(65) Prior Publication Data

US 2015/0366581 A1 Dec. 24, 2015

Related U.S. Application Data

(60) Provisional application No. 62/014,598, filed on Jun. 19, 2014.

(51) Int. Cl.
*A61B 17/00* (2006.01)
*A61N 1/05* (2006.01)
(Continued)

(52) U.S. Cl.
CPC .......... *A61B 17/00234* (2013.01); *A61B 5/06* (2013.01); *A61B 34/20* (2016.02);
(Continued)

(58) Field of Classification Search
CPC .......... A61B 17/00234; A61B 17/3421; A61B 17/3468; A61B 18/148; A61B 2090/3937;
(Continued)

(56) References Cited

U.S. PATENT DOCUMENTS

| | | | |
|---|---|---|---|
| 4,285,347 A | 8/1981 | Hess | |
| 5,419,767 A | * 5/1995 | Eggers | ................. A61B 18/149 604/114 |

(Continued)

FOREIGN PATENT DOCUMENTS

WO 2013179006 A1 12/2013

*Primary Examiner* — Peter Luong
(74) *Attorney, Agent, or Firm* — Faegre Baker Daniels LLP

(57) ABSTRACT

Various aspects describe a lead delivery system for percutaneous introduction of a lead to a stimulation site near a neural target, such as the vagus nerve for nerve stimulation. The lead delivery system may include a needle assembly having a needle adapted to cut through tissue and provide initial access into the carotid sheath. The needle may be retracted into the lead delivery system to prevent cutting structures in the carotid sheath. The lead delivery system may also include a dilator assembly having one or more dilators to dilate a path to the stimulation site. The lead delivery system may further comprise a dilator assembly including a retractable needle adapted to cut through tissue. One or more locating elements, alternatively or in addition to one or more imaging elements, may be used on individual components of the lead delivery system for enhanced trackability and locatability within the body.

13 Claims, 11 Drawing Sheets

(51) Int. Cl.
  *A61B 34/20* (2016.01)
  *G01R 33/28* (2006.01)
  *A61B 90/00* (2016.01)
  *A61B 5/06* (2006.01)
  *A61B 8/08* (2006.01)
  *A61B 18/00* (2006.01)
  *A61B 17/32* (2006.01)

(52) U.S. Cl.
  CPC ............ *A61B 90/37* (2016.02); *A61N 1/0551* (2013.01); *G01R 33/285* (2013.01); *A61B 8/0841* (2013.01); *A61B 2017/320048* (2013.01); *A61B 2018/00077* (2013.01); *A61B 2018/00083* (2013.01); *A61B 2018/00196* (2013.01); *A61B 2018/00285* (2013.01); *A61B 2018/00434* (2013.01)

(58) Field of Classification Search
  CPC .... A61B 2090/3925; A61B 2018/1432; A61B 2018/00994; A61B 2018/00351; A61B 2018/00285; A61B 2018/00196; A61B 2018/00077; A61B 2018/00083; A61B 2018/00434; A61B 2017/3433; A61B 2017/32004; A61B 8/0841; A61B 5/06; A61B 34/20; A61B 90/37; A61N 1/36053; A61N 1/36114; A61N 1/0551; G01R 33/285
  See application file for complete search history.

(56) References Cited

U.S. PATENT DOCUMENTS

| | | |
|---|---|---|
| 6,512,958 B1 | 1/2003 | Swoyer et al. |
| 6,847,849 B2 | 1/2005 | Mamo et al. |
| 7,789,833 B2 | 9/2010 | Urbano et al. |
| 7,941,227 B2 | 5/2011 | Barker |
| 8,014,873 B2 | 9/2011 | Jones et al. |
| 8,032,220 B2 | 10/2011 | Kuzma |
| 8,532,793 B2 | 9/2013 | Morris et al. |
| 2002/0151867 A1* | 10/2002 | McGuckin, Jr. ....... A61B 18/00 604/506 |
| 2005/0209564 A1* | 9/2005 | Bonner .............. A61B 17/3478 604/173 |
| 2006/0063973 A1* | 3/2006 | Makower ........... A61B 1/00135 600/114 |
| 2011/0213448 A1* | 9/2011 | Kim ................... A61B 17/3468 607/133 |
| 2013/0197615 A1 | 8/2013 | Rundle et al. |
| 2014/0148651 A1* | 5/2014 | Aman .................. A61M 29/00 600/207 |

* cited by examiner

PERCUTANEOUS TOOLS FOR MINIMALLY INVASIVE ACCESS TO THE CAROTID SHEATH FOR VAGUS NERVE STIMULATION

CROSS-REFERENCE TO RELATED APPLICATION

This application claims priority to Provisional Application No. 62/014,598, filed Jun. 19, 2014, which is herein incorporated by reference in its entirety.

TECHNICAL FIELD

The disclosure relates to systems and methods for stimulating nerves. In particular, the disclosure relates to systems and corresponding methods for delivering a stimulation lead to a target region of a vagus nerve.

BACKGROUND

The use of nerve stimulation for treating and controlling a variety of medical, psychiatric, and neurological disorders has seen significant growth over the last several decades, including for treatment of heart conditions, epilepsy, obesity, inflammatory disorders, and breathing disorders, among others. For example, modulation of the automatic balance with neural stimulation has been shown to be possible and have positive clinical benefits, such as protecting the myocardium from further remodeling and predisposition to fatal arrhythmias following a myocardial infarction (MI). Nerve stimulation often is accomplished with invasive surgical placement of a stimulating electrode adjacent to the vagus nerve. Imaging systems, such as ultrasound, are used to guide the lead to the stimulation site near the nerve during minimally invasive procedures. While Tuohy needles with echogenic features are known, there remains a continuing need for tools and methods for more accurately viewing the position and orientation of Tuohy needles and other tools for delivering a stimulation lead to a desired stimulation site near the vagus nerve and other neural targets.

SUMMARY

According to Example 1, a lead delivery system comprises a needle assembly including an outer needle and a conductive inner needle, wherein the outer needle includes a proximal end having a proximal opening, a distal end having a distal opening, a shaft defining a first lumen extending between the proximal opening and the distal opening, and a distal tip on the distal end, the distal tip being blunt and electrically conductive, the outer needle adapted to slidably receive a guidewire, wherein the conductive inner needle includes a proximal end, a distal end, a shaft extending between the proximal end and the distal end, and a sharp tip on the distal end adapted to cut tissue, the inner needle slidably received into the first lumen and electrically coupled to the distal tip of the outer needle, wherein the needle assembly is configured to protract the sharp tip from the distal opening of the outer needle to facilitate cutting tissue and to retract the sharp tip into the distal opening of the outer needle to prevent cutting tissue.

In Example 2, the lead delivery system according to Example 1 further includes a conductive wire for delivering electrical stimulation, the conductive wire electrically coupled to the distal tip of the outer needle through the inner needle.

In Example 3, the lead delivery system according to any of Examples 1-2 further includes a first locating element to assist locating the needle assembly in the body, the first locating element on one of the inner needle and the outer needle, the first locating element comprising at least one of an echogenic element and a ferromagnetic element.

In Example 4, the lead delivery system according to any of Examples 1-3 further includes an insulator on the outer needle.

In Example 5, the lead delivery system according to Example 4, wherein the insulator covers at least a portion of the echogenic element, the echogenic element being observable through the insulator by ultrasound imaging.

In Example 6, the lead delivery system according to any of Examples 1-5 further includes a second locating element comprising at least one of an echogenic element and a ferromagnetic element.

In Example 7, the lead delivery system according to any of Examples 1-6 further includes an imaging element to assist guiding the needle assembly in the body, the imaging element adapted to provide imaging information, the imaging element comprising at least one of an ultrasonic transducer and a fiber optic probe.

According to Example 8, a lead delivery system comprises a dilator assembly comprising a first dilator and a second dilator, wherein the first dilator includes a proximal end having a proximal opening, a distal end having a distal opening, a shaft defining a first lumen extending between the proximal opening and the distal opening, and a distal tip on the distal end tapering distally. The first dilator is adapted to slidably receive a guidewire in the lumen and adapted to dilate a passage in the body, and wherein the second dilator is disposed on the first dilator shaft, the second dilator adapted to further dilate the passage in the body.

In Example 9, the lead delivery system according to Example 8, wherein the dilator assembly further includes a first locating element to assist locating the dilator assembly in the body, the first locating element on one of the first dilator and the second dilator, the locating element comprising at least one of an echogenic element and a ferromagnetic element.

In Example 10, the lead delivery system according to any of Examples 8-9, wherein the dilator assembly further includes a needle including a second locating element, the needle adapted to slidably receive the guidewire, the first dilator adapted to slidably receive the needle.

In Example 11, the lead delivery system according to any of Examples 8-9 further includes the needle assembly according to Example 1, the guidewire including an electrode on a distal end of the guidewire and a blunt distal tip.

In Example 12, the lead delivery system according to any of Examples 8-11, wherein the second dilator includes a proximal end having a proximal opening, a distal end having a distal opening, a shaft defining a second lumen extending between the proximal opening and the distal opening, and a distal tip on the distal end tapering distally, the second dilator adapted to split for lateral removal.

In Example 13, the lead delivery system according to any of Examples 8-11, wherein the second dilator comprises an inflatable balloon.

In Example 14, the lead delivery system according to Example 13, wherein the inflatable balloon is disposed over the locating element, the locating element observable through the inflatable balloon by ultrasound imaging.

In Example 15, the lead delivery system according to any of Examples 8-14, wherein the dilator assembly further includes a length marker on at least one of the first and second dilators, wherein the length marker comprises at least one of a visible and a radiopaque material.

According to Example 16, a needle assembly for introducing a guidewire into a body comprises an outer needle including a proximal end having a proximal opening, a distal end having a distal opening, a shaft defining a first lumen extending between the proximal opening and the distal opening, and a distal tip on the distal end, the distal tip being blunt and electrically conductive, the outer needle adapted to slidably receive a guidewire; a conductive inner needle including a proximal end, a distal end, a shaft, and a sharp tip on the distal end adapted to cut tissue, the inner needle slidably received into the first lumen and electrically coupled to the distal tip of the outer needle, wherein the needle assembly is configured to protract the sharp tip from the distal opening of the outer needle to facilitate cutting tissue and to retract the sharp tip into the distal opening of the outer needle to prevent cutting tissue; a conductive wire for delivering electrical stimulation, the conductive wire electrically coupled to the distal tip of the outer needle through the inner needle; and a first locating element to assist locating the needle assembly in the body, the first locating element on one of the inner needle and the outer needle, the first locating element comprising at least one of an echogenic element and a ferromagnetic element.

In Example 17, the needle assembly according to Example 16 further includes an insulator on the outer needle.

In Example 18, the needle assembly according to Example 17, wherein the insulator covers at least a portion of the echogenic element, the echogenic element observable through the insulator by ultrasound imaging.

In Example 19, the needle assembly according to any of Examples 16-18 further includes a second locating element comprising at least one of an echogenic element and a ferromagnetic element.

In Example 20, the needle assembly according to any of Examples 16-19 further includes an imaging element to assist guiding the needle assembly in the body, the imaging element adapted to provide imaging information, the imaging element comprising at least one of an ultrasonic transducer and a fiber optic probe.

According to Example 21, a dilator assembly for introducing a lead into a body comprises a first dilator including a proximal end having a proximal opening, a distal end having a distal opening, a shaft defining a first lumen extending between the proximal opening and the distal opening, and a distal tip on the distal end tapering distally, the first dilator adapted to slidably receive a guidewire and adapted to dilate a passage in a body; a second dilator on the first dilator shaft, the second dilator adapted to further dilate the passage in the body; and a first locating element to assist locating the dilator assembly in the body, the first locating element on one of the first dilator and the second dilator, the locating element comprising at least one of an echogenic element and a ferromagnetic element.

In Example 22, the dilator assembly according to Example 21 further includes a needle having a second locating element, the needle adapted to slidably receive a guidewire, the first dilator adapted to slidably receive the needle.

In Example 23, the dilator assembly according to any of Examples 21-22 further includes a guidewire having a blunt distal tip and adapted to tunnel through the interior of a sheath in the body, the guidewire including an electrode on a distal end of the guidewire.

In Example 24, the dilator assembly according to any of Examples 21-23, wherein the second dilator includes a proximal end having a proximal opening, a distal end having a distal opening, a shaft defining a second lumen extending between the proximal opening and the distal opening, and a distal tip on the distal end tapering distally, the second dilator adapted to split for lateral removal.

In Example 25, the dilator assembly according to any of Examples 21-23, wherein the second dilator comprises an inflatable balloon.

In Example 26, the dilator assembly according to Example 25, wherein the inflatable balloon is disposed over the locating element, the locating element observable through the inflatable balloon by ultrasound imaging.

In Example 27, the dilator assembly according to any of Examples 21-26 further includes a length marker on at least one of the first and second dilators, wherein the length marker comprises at least one of a visible material and a radiopaque material.

According to Example 28, a method of introducing a stimulation lead into a body with a lead delivery system, the body having tissue and a sheath, the sheath having an interior and a stimulation site within the interior, comprises advancing a first needle subcutaneously through tissue toward and into the sheath in the body; advancing a guidewire having a blunt distal tip along the interior of the sheath to a stimulation site; testing the stimulation site using an electrode on at least one of the first needle and the guidewire; advancing a first dilator on the guidewire along the interior of the sheath toward a stimulation site to dilate a path; and observing the first dilator in the body using at least one of a locating element and an imaging element on the first dilator.

In Example 29, the method according to Example 28, further comprises retracting the first needle into the lead delivery system to prevent the first needle from cutting tissue; advancing the second needle along the interior of the sheath to the stimulation site; observing the second needle in the body using at least one of a locating element and an imaging element on the needle; removing the first needle from the body before advancing the guidewire to the stimulation site; and removing the second needle from the body after advancing the guidewire to the stimulation site.

In Example 30, the method according to Example 29, further comprises advancing a second dilator on the first dilator along the interior of the sheath toward the stimulation site; removing the first dilator and the guidewire from the body; advancing a stimulation lead to the stimulation site; and splitting the second dilator for lateral removal.

In Example 31, the method according to Example 29, further comprises inflating a dilating balloon on the first dilator; deflating the dilating balloon; removing the first dilator and dilating balloon from the body; advancing a stimulation lead to the stimulation site over the guidewire; and removing the guidewire from the body.

In Example 32, the method according to Example 28, further comprises removing the first needle from the body; advancing a second dilator on the first dilator along the interior of the sheath toward the stimulation site; removing the first dilator and the guidewire from the body; advancing a stimulation lead to the stimulation site; and splitting the second dilator for lateral removal.

In Example 33, the method according to Example 28 further comprises removing the first needle from the body; inflating a dilating balloon on the first dilator; deflating the dilating balloon; removing the first dilator and inflatable balloon from the body; advancing a stimulation lead to the stimulation site over the guidewire; and removing the guidewire from the body.

In Example 34, the method according to Example 29, wherein testing the stimulation site comprises electrically stimulating the stimulation site through the first needle and a distal end of the second needle.

In Example 35, the method according to Example 28, wherein testing the stimulation site comprises electrically stimulating the stimulation site through an electrode on a distal end of the guidewire.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
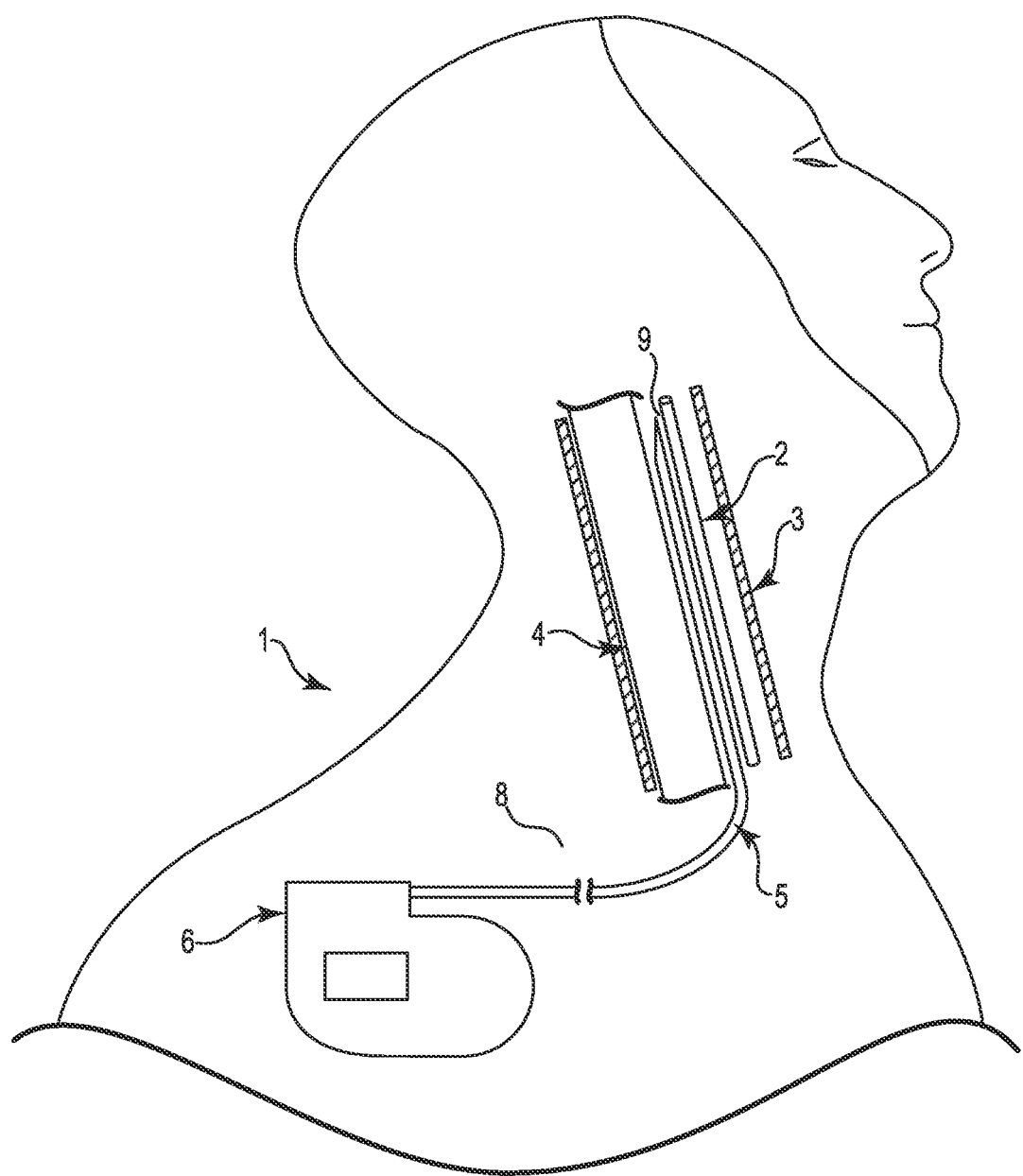
FIG. 1 is a schematic illustration of a system for stimulating a region of a patient's vagus nerve located within a carotid sheath according to an embodiment.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration showing a system 1 for stimulating a region of a patient's vagus nerve 2 located within a carotid sheath 3 (shown in cross-section in FIG. 1). As is known, the carotid sheath 3 consists of multiple layers of fascia in its interior, which wrap around the internal jugular vein (IJV) 4 and the vagus nerve 2. Between the skin and carotid sheath 3 of a human body lies tissue 8, such as muscle tissue.

As shown, the system 1 includes a lead 5 and an implantable pulse generator 6. In the illustrated embodiment, the lead 5 is placed at a stimulation site 9 adjacent to and parallel to the vagus nerve 2, and the lead 5 is coupled to the pulse generator 6. In various embodiments, the system 1 can be used to selectively stimulate the vagus nerve 2 for treating cardiac disease. As such, in various embodiments, the lead 5 includes electrodes (not shown in FIG. 1) that are electrically and operatively coupled to electronics of the pulse generator 6 to deliver electrical stimuli to the vagus nerve 2 when implanted. In various embodiments, the lead 5 may be implanted in a minimally-invasive manner by subcutaneously tunneling a path between the implantation site of the pulse generator 6 and the stimulation site 9 using delivery tools according to the various embodiments described herein. Such delivery tool embodiments can include, among other things, novel needle and dilator assemblies and tunneling tools (e.g., guidewires), described herein.

Figure 2:
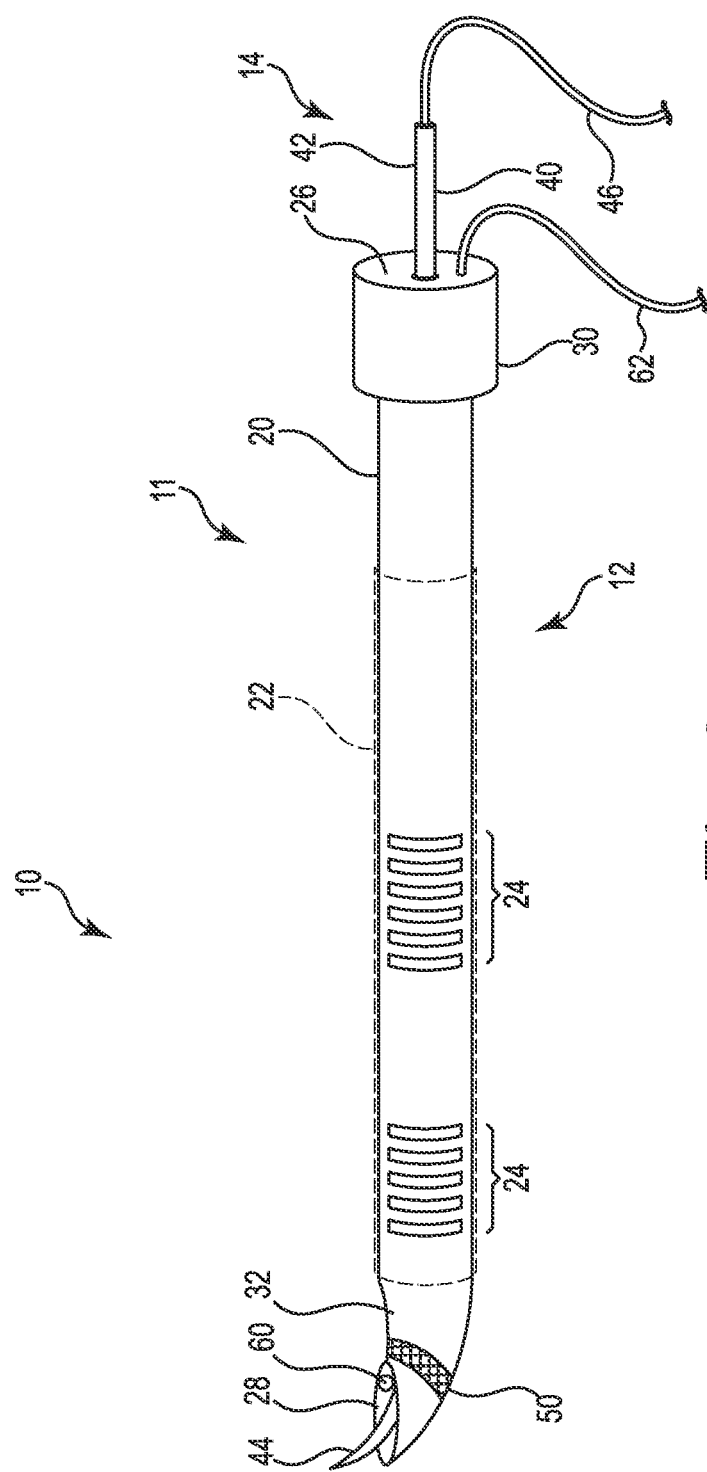
FIG. 2 is a schematic illustration of a lead delivery system including a needle assembly for introducing a lead to a stimulation site, according to some embodiments.

FIG. 2 is a schematic illustration showing a portion of a lead delivery system 10 including a needle assembly 11, according to some embodiments. The lead delivery system includes various percutaneous tools for minimally invasive access to a neural target, such as the carotid sheath for vagus nerve stimulation. The needle assembly 11 is configured to provide initial access by forming an initial path to the target site within the patient tissue. For example, the needle assembly 11 can form an initial path for a dilator assembly to further dilate the path before introducing a lead 5. In the illustrated embodiment, the needle assembly 11 is adapted to deliver a guidewire (e.g., tunneling tool) to the stimulation site 9. In various embodiments, the needle assembly 11 is adapted to pierce the patient's skin, advance through the tissue 8, pierce the carotid sheath 3, and tunnel through the interior of the carotid sheath 3 to the stimulation site 9 (e.g., see FIG. 1). In the embodiment shown, the needle assembly 11 includes an outer needle 12 and an inner needle 14 at least partially disposed within outer needle 12.

The outer needle 12 includes a shaft 20, a proximal end 30, and a distal end 32. In one embodiment, the shaft 20 is tubular and extends longitudinally between the proximal and distal ends 30, 32. As shown, a proximal opening 26 is formed in the proximal end 30, and a distal opening 28 is formed in the distal end 32. The shaft 20 defines a first lumen (not shown) extending between the proximal and distal openings 26, 28.

In the illustrated embodiment, the shaft 20 has a generally cylindrical cross-sectional shape extending longitudinally. In other embodiments, the shaft 20 may have different cross-sectional shapes (e.g., rectangular, octagonal, elliptical, crescent, and the like).

As further shown, in the illustrated embodiment, the proximal end 30 has a larger lateral width as compared to the lateral width of the distal end 32, so as to facilitate easy grasping and manipulation of the proximal end 30 by a user of the needle assembly 11. In one embodiment, the outer needle 12 is configured as a Tuohy needle, wherein at least a portion of the distal end 32 is curved relative to the remainder of the shaft 20.

In various embodiments, the needle assembly 11 includes features to assist the user in visualizing, locating and navigating the needle assembly 11 within the patient's tissue during minimally invasive procedures. Such features may include various locating elements, markers, navigation aids, and the like.

In one embodiment, the needle assembly 11 includes one or more locating elements that can allow the needle assembly 11 to be located and/or tracked inside the body during minimally invasive procedures. In the illustrated embodiment, the locating elements can include one or more echogenic elements 24 that can allow the needle assembly 11 to be visualized using ultrasound imaging. In the particular embodiment illustrated, the outer needle 12 includes a plurality of echogenic elements 24 longitudinally spaced along the shaft 20.

The one or more echogenic elements 24 can be formed using any suitable construction that enhances their visibility under ultrasound, such that they can be distinguished under ultrasound from other features on the needle assembly 11. In some embodiments, the one or more echogenic elements 24 can be formed by the addition of physical features (e.g., grooves, microbubbles, etc.) in the shaft 20 of the outer needle 12. In various embodiments, the one or more echogenic elements 24 can be integrally formed in the shaft 20. In other embodiments, the echogenic elements can be formed separately from the shaft 20 and attached to the shaft 20 during manufacture thereof.

In the illustrated embodiments, the needle assembly 11 includes a plurality of groups (e.g., two groups) of one or more echogenic elements 24, with the groups being longitudinally spaced from one another on the shaft 20 of the outer needle 12. In one embodiment, the relative spacing between the respective groups of one or more echogenic elements 24 can provide the user with additional information about the position and/or orientation of the needle assembly 11 under ultrasound imaging. In various embodiments, the groups of one or more echogenic elements 24 can have different configurations from one another (e.g., using different echogenic features, more/fewer grooves, different densities of microbubbles, etc.). It should be understood that, although in the illustrated embodiment two groups of one or more echogenic elements 24 are shown, in other embodiments, more or fewer groups can be included. In still other embodiments, the one or more echogenic elements 24 need not be formed into groups, but can be spaced along the length of the shaft 20 in a desired manner (where more than one echogenic element 24 is utilized). In various other embodiments, the echogenic elements 24 can be provided on other components of the lead delivery system 10 in lieu of, or in addition to, the outer needle 12.

In the illustrated embodiment, the needle assembly 11 further includes an additional locating element in the form of a ferromagnetic element 50 for use of the needle assembly 11 in conjunction with a magnetic-based tracking and navigation system. In the embodiment shown, the ferromagnetic element 50 is disposed on the distal end 32 of the outer needle 12. In various embodiments, the needle assembly 11 can include additional ferromagnetic elements on other locations of the outer needle 12 or other components of the needle assembly 11. The inclusion of the ferromagnetic element 50 can enable concurrent use of ultrasound imaging and magnetic-based tracking of the needle assembly 11. In one embodiment, the ferromagnetic element 50 is a passive component that can be detected by an external system when a magnetic field is applied thereto. In one such embodiment, the ferromagnetic element 50 is a foil ring made of a ferromagnetic material. As shown in FIG. 2, the ferromagnetic element 50 is a foil ring integrated into the material of the outer needle 12 on the distal end 3. In other embodiments, the ferromagnetic element 50 may be a magnetic sensor configured for sensing an externally-generated magnetic field and to provide an output signal for use in tracking the position and orientation of the needle assembly 11 in the patient's body. Such a magnetic sensor can be coupled to an external system by any suitable known method, such as through a cable or conductor wire. As shown, cable 62 extends outwardly from the proximal end 30 of the outer needle 12 from a passage (not shown) through the outer needle.

As further shown in FIG. 2, in some embodiments, an imaging element 60 is included on the needle assembly 11 to assist guiding the needle assembly 11 in the body by enabling imaging of the internal anatomical features during minimally invasive procedures. For example, the imaging element 60, when present, can be used to visualize the proximity of the needle assembly 11 to other structures in the body. In some embodiments, the imaging element 60 comprises an ultrasonic transducer providing and receiving ultrasonic signals to form imaging information. In some embodiments, the imaging element 60 comprises a fiber optic probe for providing and receiving light to form imaging information. In some embodiments, the imaging element 60 comprises one or more ultrasonic transducers and one or more fiber optic transducers enabling concurrent use of both imaging techniques. The imaging element 60 can be placed anywhere in or on the needle assembly 11 where visibility exterior to the needle assembly 11 is desirable. The imaging element 60, as shown, is disposed within the distal end 32 of the outer needle 12 allowing visibility beyond a distal tip of the needle assembly 11. Imaging element 60 can be operatively coupled to external imaging equipment (not shown) by any known suitable method, such as by a cable similar to cable 62.

The one or more locating elements, e.g., the echogenic elements 24 and/or the ferromagnetic element 50, and the one or more imaging elements 60, when present, can be used together to facilitate locating and guiding the needle assembly 11 as it advances through the body.

In some embodiments, the outer needle 12 is made of an electrically conductive material in order to enable the outer needle 12 to be electrically coupled to the external environment and thus operate as an electrode. In the embodiment shown, the needle assembly 11 includes an insulator 22 on the outer needle 12 to electrically isolate the shaft 20 of the outer needle 12 from the adjacent environment. As shown, the insulator 22 does not cover the distal end 32, which leaves the distal end 32 electrically coupled to the respective adjacent environment. The insulator 22 can be formed of any suitable biocompatible material, such as silicone, polyurethane, and/or ethylene tetrafluoroethylene (ETFE), for example. In the embodiment shown, the insulator 22 covers the echogenic elements 24 while being observable through the insulator by ultrasound imaging, allowing for enhanced visibility during ultrasound imaging.

The inner needle 14 is at least partially disposed in the lumen of the outer needle 12 and includes a shaft 40, a proximal end 42, and a distal end 44, with the shaft 40 extending between the proximal and distal ends 42, 44. In the illustrated embodiment, the distal end 44 includes a sharp tip. A sharp tip can be adapted to cut through tissue 8 and pierce the carotid sheath 3 when advanced. The inner needle 14 is adapted to be both extendable and retractable within the outer needle 12. As shown, the distal end 44 can be extendable from the distal opening 28 of the outer needle 12, such that a sharp tip (when present) of the distal end 44 of the inner needle 14 extends beyond the distal end 32 of the outer needle 12. In some embodiments, the inner needle 14 is further adapted to retract into the distal opening 28 of the outer needle 12. While retracted, the distal end 44 of the inner needle 14 does not extend beyond the distal end 32 of the outer needle 12. The inner needle 14 can be made out of any suitable biocompatible material.

In some embodiments, the inner needle 14 is made of an electrically conductive material. In the illustrated embodiment, the conductive inner needle 14 is attached and electrically coupled to conductive wire 46 extending from the proximal end 42, which in turn can be operatively coupled to an external medical device such as a pacing system analyzer or pacing pulse generator (not shown). In such embodiments, electrical stimulation can be delivered through the conductive wire 46 to the conductive inner needle 14. In some embodiments with a conductive distal end 32 of the outer needle 12, the electrical stimulation can be delivered to the conductive distal end 32 through the inner needle 14 from the conductive wire 46, enabling testing of the stimulation site 9 near the vagus nerve 2 with the needle assembly 11. In some embodiments, the inner needle 14 is electrically coupled to the conductive distal end 32 of the outer needle 12 through a conductive element (not shown), such as a brush or a spring disposed between the inner needle 14 and the outer needle.

In some embodiments, the inner needle 14 may be retracted and removed from the proximal opening 26 of the outer needle 12 enabling a guidewire to enter the proximal opening 26 and be fed through the lumen out the distal opening 28 of the outer needle. This allows placement of the distal end of the guidewire near the stimulation site 9. After placement of the guidewire, a dilator assembly can be used to dilate a passage in the carotid sheath before placing the lead 5.

Figure 3:
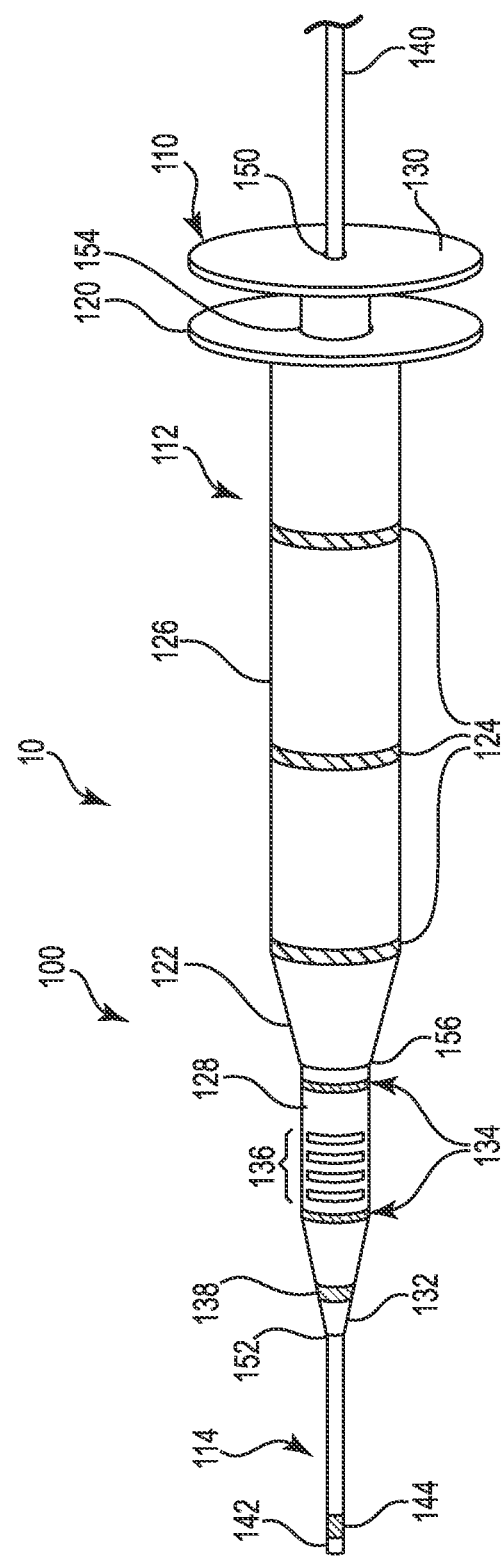
FIG. 3 is a schematic illustration of a lead delivery system including a dilator assembly for introducing a lead to a stimulation site, according to some embodiments.

FIG. 3 is a schematic illustration showing a portion of the lead delivery system 10 including a dilator assembly 100 on a guidewire 114 (i.e., tunneling tool) adapted to dilate a passage in the body after placement of the guidewire, according to some embodiments. The dilator assembly 100 can be used after using needle assembly 11 to place guidewire 114. As shown, the dilator assembly 100 extends longitudinally and includes an inner dilator 110 on the guidewire 114 and an outer dilator 112 on the inner dilator 110.

In some embodiments, as shown, the guidewire 114 has a proximal end 140 and a distal end 142. In some embodiments, the distal end 142 has a blunt distal tip which can be adapted to prevent cutting tissue or structures within the body, particularly within the carotid sheath. In some embodiments, the guidewire 114 is adapted to be somewhat flexible, yet rigid enough to tunnel through the fascia on the interior of the carotid sheath for placement adjacent to the vagus nerve 2. In the illustrated embodiment, the guidewire 114 includes an electrode 144 on the distal end 142, which enables testing of the stimulation site 9 near the vagus nerve 2 with the dilator assembly 100. In other embodiments, the electrode 144 is omitted.

The inner dilator 110 is adapted to slidably receive the guidewire 114 and dilate a passage in a body. As shown, the inner dilator 110 includes a shaft 128, a proximal end 130, and a distal end 132. The shaft 128 extends from proximal end 130 to distal end 132. The shaft 128 further defines a first lumen (not shown) extending between a proximal opening 150 formed in proximal end 130 and a distal opening 152 formed in distal end 132. In the embodiment shown, the guidewire 114 extends through the first lumen and protrudes through the proximal opening 150 and distal opening 152. In some embodiments, the distal end 132 has a distal tip tapering distally from the shaft 128 allowing the inner dilator 110 to gradually increase the lateral width of the passage in the body as the inner dilator 110 is advanced through the body.

In some embodiments, the inner dilator 110 is adapted to be splittable to allow for lateral removal of the inner dilator 110 from the guidewire 114 when the guidewire 114 is disposed within the inner dilator 110. The proximal end 130 can be adapted to be gripped by a user of the dilator assembly 100, in the embodiment shown.

The dimensions of the inner dilator 110 can be varied according to the clinical requirements for the dilator assembly 100. In one embodiment, the shaft 128 of the inner dilator 110 is about 4 French (4 F). In some embodiments, the proximal end 130 has a width greater than the shaft 128, which can further enhance the handling characteristics of the inner dilator 110.

The outer dilator 112 is adapted to further dilate the passage in the body, in some embodiments. As shown, the outer dilator 112 is on the inner dilator 110. Also, as shown, the outer dilator 112 includes a proximal end 120, a distal end 122, and a shaft 126 extending between the proximal and distal end. The proximal end 120 includes a proximal opening 154 formed in proximal end, and the distal end 122 includes a distal opening 156 formed in distal end 122. The shaft 126 includes a second lumen (not shown) extending between the proximal opening 154 and the distal opening 156. In the embodiment shown, the inner dilator 110 extends through the second lumen and protrudes through the proximal opening 154 and distal opening 156.

In some embodiments, the distal end 122 forms a distal tip tapering distally from the shaft 126 allowing the dilator to gradually increase the lateral width of the passage in the body as the outer dilator 112 is advanced through the body. In the embodiment shown, the shaft 126 of outer dilator 112 has a greater diameter than shaft 128 of the inner dilator 110. In some embodiments, the outer dilator 112 is adapted to be splittable to allow for lateral removal from the inner dilator 110 or from the guidewire 114 when the guidewire 114 is disposed within the inner dilator 110.

In various embodiments, the inner and outer dilators 110, 112 are made of any suitable biocompatible material known to those having skill in the art, such as, for example, polytetrafluoroethylene (PTFE), fluorinated ethylene propylene (FEP), ETFE, polyurethane, nylon, Pebax, polyetheretherketone (PEEK), or any combination of these materials. In some embodiments, one or more dilators 110, 112 are made of a flexible material with sufficient stiffness to provide pushability in-situ with hands or surgical tools without creating undue trauma to nearby tissues. In other embodiments, one or more dilators 110, 112 are made of a rigid material.

The dimensions of the outer dilator 112 can be varied according to the clinical requirements for the dilator assembly 100. In one embodiment, the shaft 126 of the outer dilator 112 is about 6 French. The proximal end 120 is adapted to be gripped by a user of the dilator assembly 100, in the embodiment shown. In some embodiments, the proximal end 120 has a width greater than the shaft 126.

In the illustrated embodiment, the dilator assembly 100 includes an echogenic element 136 for enhanced visibility during ultrasound imaging, similar to echogenic elements 24 on the needle assembly 11. As shown, in the illustrated embodiment, the echogenic element 136 is on the shaft 128 of the inner dilator 110, and located such that the distal end 122 of the outer dilator 112 is disposed proximal the echogenic element 136. In the illustrated embodiment, the dilator assembly 100 includes a single echogenic element 136. In other embodiments, the dilator assembly 100 may include a plurality of echogenic elements 136, which may be grouped or otherwise configured, similar to the echogenic elements 24 of the needle assembly 11, to provide the user with enhanced information regarding the position and/or orientation of the dilator assembly 100 during minimally invasive procedures.

As further shown, in the illustrated embodiment, the dilator assembly 100 includes a ferromagnetic element 138 for enhanced visibility during magnetic-based tracking and navigation, similar to ferromagnetic element 50 of the needle assembly 11. In the various embodiments, the ferromagnetic element 138 can have substantially the same or identical configuration as the ferromagnetic element 50 of the needle assembly 11. As shown, the ferromagnetic element 138 is a foil ring integrated into the material of the inner dilator 110 on the distal end 132. In other embodiments, the ferromagnetic element 138 may be a magnetic sensor configured for sensing an externally-generated magnetic field and to provide an output signal for use in tracking the position and orientation of the needle assembly 11 in the patient's body. Such a magnetic sensor can be coupled to an external machine by any suitable known method, such as through a cable or conductor wire (not shown) similar to cable 62.

In some embodiments, the dilator assembly 100 includes length markers 124, 134 to assist insertion depth of the dilator assembly on at least one of the inner dilator 110 and the outer dilator 112. The length markers may be configured to have enhanced radiopacity relative to the adjacent portions of the inner or outer dilators 110, 112 on which they are disposed, so as to be readily identifiable under fluoroscopy. As shown, the length markers 134 are rings that are longitudinally spaced on the shaft 128 of the inner dilator 110. Also, as shown, the length markers 124 are rings that are longitudinally spaced on the shaft 126 of outer dilator 112. When present, the length markers 124, 134 may be spaced between 1 to 10 centimeters apart. In some embodiments, the length markers 124, 134 may be spaced 2 to 5 centimeters apart. Other shapes of length markers other than rings may be used, as well. In some embodiments, as shown, one or more length markers are adjacent to the echogenic element 136 or the ferromagnetic element 138.

The one or more echogenic elements 136, one or more ferromagnetic elements 138, electrode 144, and length markers 124, 134 provide trackability and locatability of the dilator assembly 100 as it advances through the body.

Figure 4:
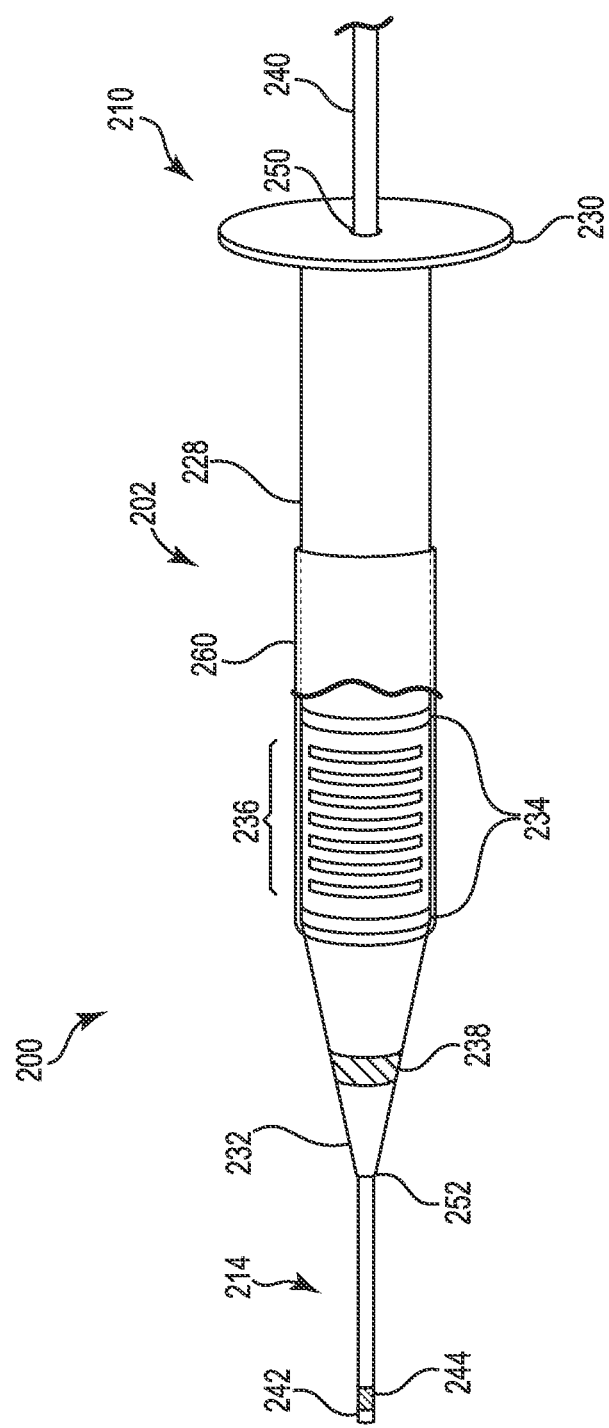
FIG. 4 is a schematic illustration of a lead delivery system including a dilator assembly for introducing a lead to a stimulation site, according to alternative embodiments.

FIG. 4 is a schematic illustration showing a portion of a lead delivery system 200 including a dilator assembly 202 on a guidewire (i.e., tunneling tool) 214 adapted to dilate a passage in the body, according to alternative embodiments. Dilator assembly 202 may be used as an alternative to dilator assembly 100 after using needle assembly 11 to place guidewire 214. The dilator assembly 202 is, except as described herein, similar to the dilator assembly 100, and includes a single dilator 210 on a guidewire 214. As shown, the dilator 210 includes a shaft 228, a proximal end 230, and a distal end 232, wherein the shaft 228 extends between the distal and proximal ends 230, 232. As further shown, the shaft 228 includes a proximal opening 250 formed in the proximal end 230, and a distal opening 252 formed in the distal end 232. Additionally, the shaft 228 defines a first lumen (not shown) extending between the proximal opening 250 and the distal opening 252.

In the illustrated embodiment, the guidewire 214 includes a proximal end 240, a distal end 242, and an electrode 244 proximate the distal end 242. Also, as further shown, the guidewire 214 includes a plurality of length markers 234, an echogenic element 236, and/or a ferromagnetic element 238. Each may be of similar construction and provide similar or identical functionality as length markers, echogenic elements, and ferromagnetic elements on the needle assembly 11 and/or the dilator assembly 100.

In the illustrated embodiment, the dilator assembly 202 differs from dilator assembly 100, however, in that the dilator 210 includes a balloon 260 disposed over the shaft 228. As shown, the balloon 260 is cutaway to show echogenic element 236. In various embodiments, the balloon 260 is adapted so as to be inflatable within the carotid sheath to further dilate the passage dilated by the dilator 210. For example, the dilator assembly 202 may include an internal lumen (not shown) to supply a fluid to inflate or deflate balloon 260. The inflated balloon 260 can be deflated to enable removal of the dilator assembly 202 from the passage and the body. In some embodiments, as shown in FIG. 4, the balloon 260 is disposed over the echogenic element 236, which is observable through balloon 260 by ultrasound imaging, allowing the location of the balloon 260 to be identified by ultrasonic imaging. The balloon 260 may be made of any suitable biocompatible material that is expandable known to those having skill in the art, such as Nylon, Silicone, Pebax, PET, polyurethane, or a combination of these materials.

Figure 5:
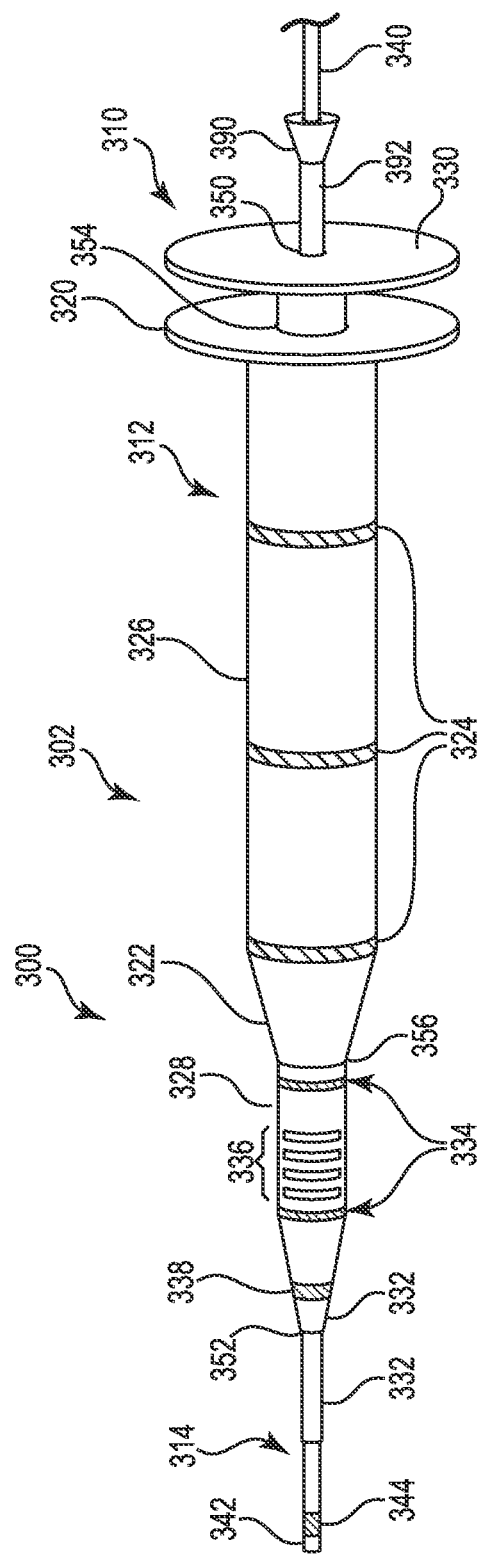
FIG. 5 is a schematic illustration of a lead delivery system including a dilator assembly including a needle, according to some embodiments.

FIG. 5 is a schematic illustration showing a lead delivery system 300 including a dilator assembly 302 that includes a needle 390, according to some embodiments. Lead delivery system 300 can be used as an alternative to lead delivery system 10. The dilator assembly 302 is similar to dilator assembly 100 and is numbered accordingly for similar elements, and includes an inner dilator 310, an outer dilator 312, and a guidewire 314. As shown, the inner dilator 310 includes a shaft 328, a proximal end 330 and a distal end 332, with the shaft 328 extending between the proximal and distal ends 330, 332 and defining a first lumen (not shown) therethrough. The proximal end 330 has a proximal opening 350, the distal end 332 has a distal opening 352, and the first lumen (not shown) extends from the proximal opening 350 through the distal opening 352.

As further shown, the outer dilator 312 includes a proximal end 320, a distal end 322, and a shaft 326 extending between the proximal and distal ends 320, 322. Additionally, the outer dilator 312 includes a proximal opening 354 formed in the proximal end 320, and a distal opening 356 formed in the distal end 322, and the second lumen (not shown) extends from the proximal opening 354 through the distal opening 356.

As also shown, the guidewire 314 includes a proximal end 340, a distal end 342, and an electrode 344 proximate the distal end 342. Additionally, in the illustrated embodiment, the dilator assembly 302 includes a plurality of length markers 324, 334, an echogenic element 336, and/or a ferromagnetic element 338, each of which may be included or omitted, and each of which, when present, can have substantially the same or identical construction and/or functionality as the corresponding features on the needle assembly 11 and the dilator assemblies 100, 202.

The dilator assembly 302 differs from the dilator assembly 100 at least in that the dilator assembly 302 includes the needle 390, which as shown has a proximal end 392 and a distal end 394. In this configuration, the dilator assembly 302 is adapted to introduce lead 5 to stimulation site 9 without a separate needle assembly 11 to establish initial access to the implantation site. The needle 390 is adapted to cut through tissue such that the tissue is less moved and deformed than using a dilator assembly without a needle. As shown, the guidewire 314 is slidably received into needle 390, and the needle 390 is slidably received into the inner dilator 310. In some embodiments, the needle 390, or a portion thereof, is echogenic. For example, in one embodiment, the needle 390 is an echogenic Tuohy needle. Furthermore, in various embodiments, the one or more echogenic elements 336, ferromagnetic elements 338, electrode 344, and length markers 324 and 334 provide trackability and locatability of the dilator assembly 302 as it advances through the body.

Figure 6:
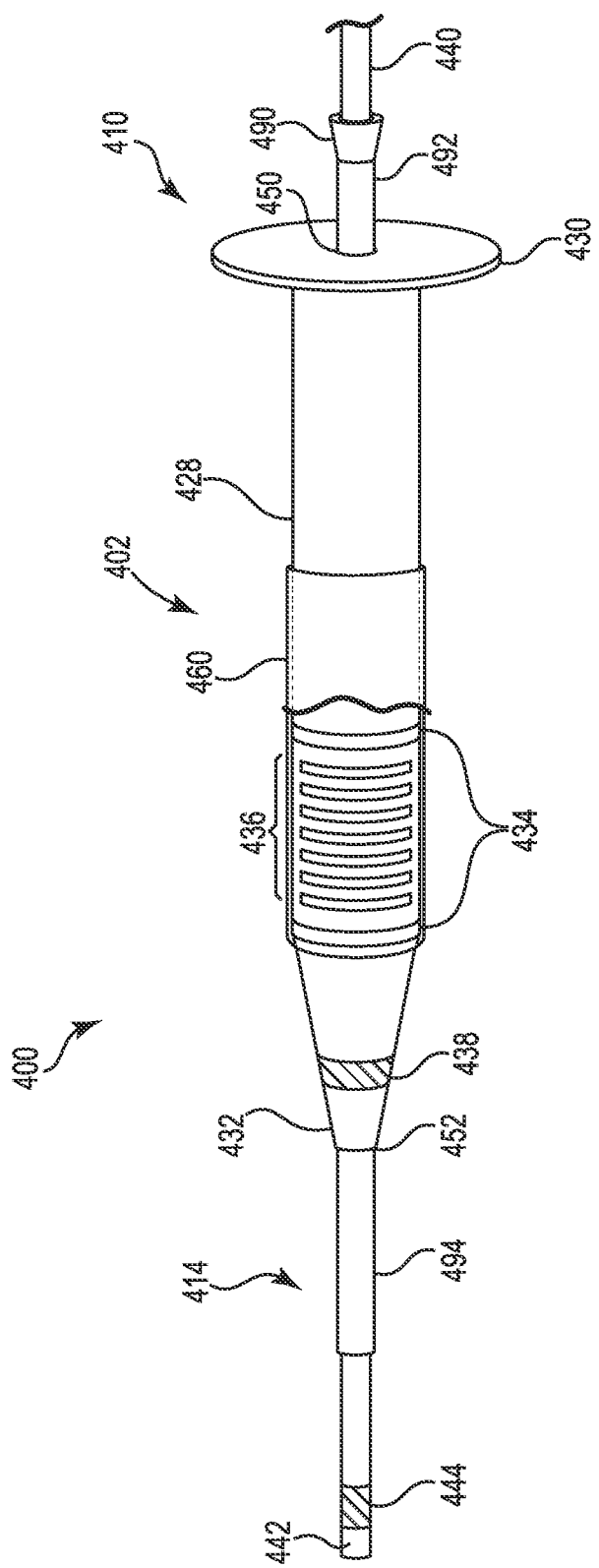
FIG. 6 is a schematic illustration of a lead delivery system including a dilator assembly including a needle, according to alternative embodiments.

FIG. 6 is a schematic illustration of a lead delivery system 400 including a dilator assembly 402 that includes a needle 490, according to alternative embodiments. The lead delivery system 400 can be used as an alternative to lead delivery system 10. The dilator assembly 402 is similar to the dilator assembly 202 and is numbered accordingly for similar elements, and includes a single dilator 410 and a guidewire 414 (i.e., tunneling tool). As shown, the dilator 410 includes a shaft 428, a proximal end 430 and a distal end 432, with the shaft 428 extending between the proximal and distal ends 430, 432. As further shown, the dilator 410 has a proximal opening 450 formed in proximal end 430, and a distal opening 452 formed in distal end 432. Additionally, the shaft 428 includes a first lumen (not shown) extending from the proximal opening 450 through the distal opening 452. Also, the guidewire 414 includes a proximal end 440, a distal end 442, and an electrode 444 proximate the distal end 442.

Additionally, similar to the dilator assembly 202, the dilator assembly 402 includes a balloon 460 disposed about the shaft 428 of the dilator 410. As shown, the balloon 460 is shown in a cutaway view to show echogenic element 436 disposed on the shaft 428 of the dilator 410. The dilator assembly 402 may include an internal lumen (not shown) to supply a fluid to inflate or deflate balloon 460. As further shown, the dilator assembly 402 includes length markers 434 and one or more locating elements, such as echogenic element 436 and ferromagnetic element 438, each of which can have substantially the same or identical construction and/or functionality as the corresponding elements of the dilator assembly 202.

The dilator assembly 402 differs from dilator assembly 202 at least in that the needle 490 is included, which has a proximal end 492 and distal end 494, similar to needle 390. In this configuration, the dilator assembly 402 is adapted to introduce the lead 5 to stimulation site 9 without a separate needle assembly, such as the needle assembly 11, to provide initial access to the site. The needle 490 is adapted to cut through tissue such that the tissue is less moved and deformed than using a dilator assembly without a needle. In various embodiments, the guidewire 414 (i.e., tunneling tool) is slidably received into needle 490, and the needle 490 is slidably received into the first dilator 410. In some embodiments, needle 490 is echogenic. For example, in some embodiments, the needle 490 is an echogenic Tuohy needle. Furthermore, the locating elements (e.g., the one or more echogenic elements 436 and the one or more ferromagnetic elements 438), length markers 434, and electrode 444, can provide trackability and locatability of the dilator assembly 402 as it is advanced through the body.

Figure 7:
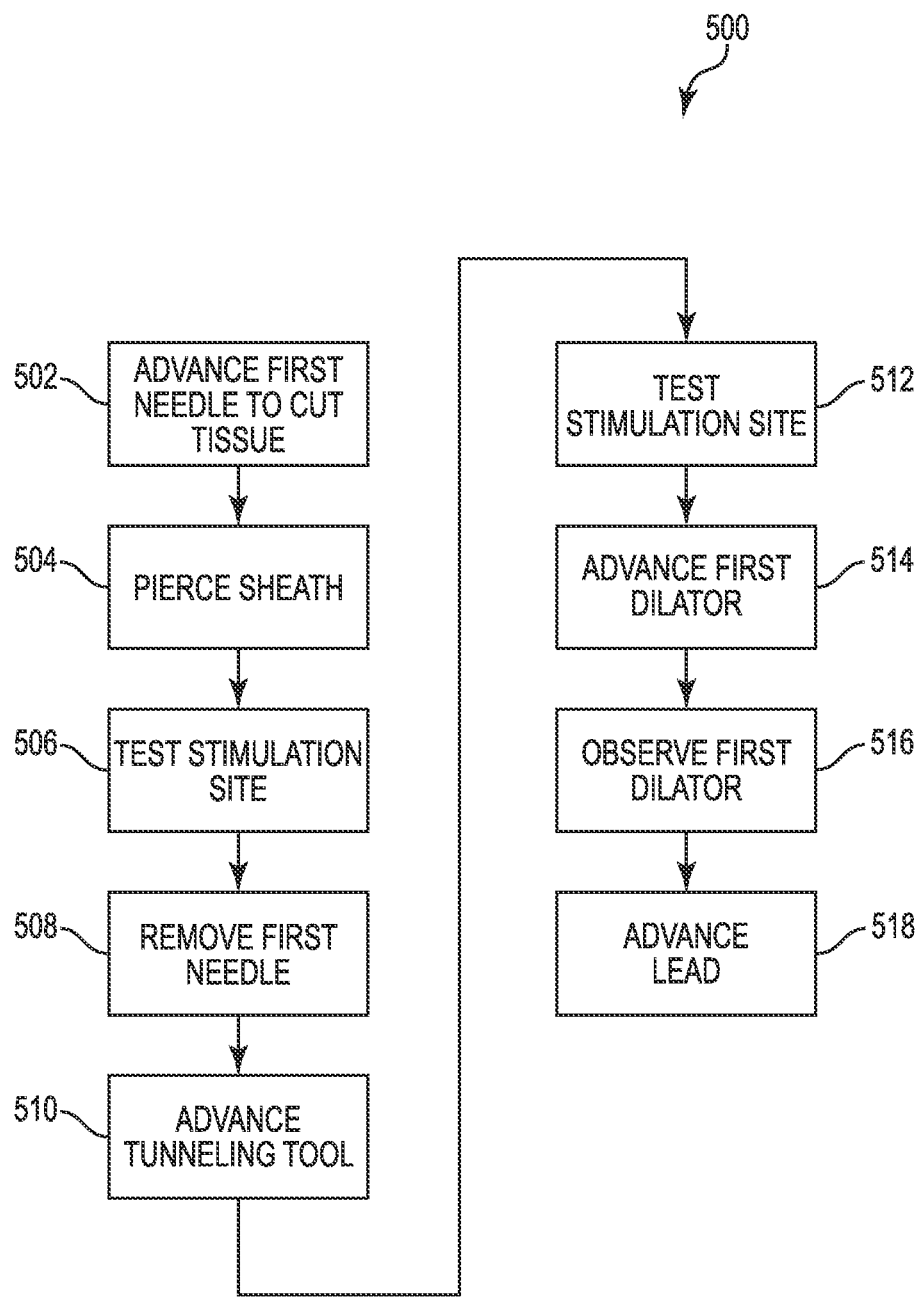
FIG. 7 is a flow diagram of an exemplary method for introducing a lead to a stimulation site, according to some embodiments.

FIG. 7 is a flow diagram of an exemplary method 500 of using a lead delivery system for introducing a stimulation lead to a stimulation site 9, according to some embodiments.

In step 502, a first needle is advanced through a body to cut through tissue, such as muscle tissue. The first needle is adapted to cut through tissue such that the tissue is less moved and deformed as the first needle is advanced as compared to when a dilator is advanced through the tissue without the first needle. In some embodiments, a second needle is advanced with the first needle in step 502. In step 504, a sheath within the body is pierced, such as the carotid sheath 3, by the first needle. In step 506, the stimulation site 9 is electrically tested by the first needle, specifically the distal end of the first needle, to verify the stimulation site 9 near the vagus nerve 2. A physiological response that verifies capture of the vagus nerve can be obtained and typically elicits vibration of the laryngeal muscles, a decrease in heart rate or a deep breath respiratory response. In other embodiments, step 506 is omitted. In step 508, the first needle is removed. In other embodiments, when a second needle is not introduced with the first needle, step 510 precedes step 508 allowing the guidewire to track the path of the first needle before its removal.

In step 510, a guidewire (i.e., tunneling tool) is advanced in the interior of the carotid sheath 3 to the stimulation site 9. In various embodiments, the inner needle is not advanced through the interior of the carotid sheath 3. In step 512, the stimulation site 9 is electrically tested by the guidewire, specifically an electrode on the guidewire to verify the stimulation site 9 near the vagus nerve 2. In other embodiments, step 512 is omitted. In step 514, a first dilator having at least one locating element is advanced, in particular, through the interior of the sheath toward the stimulation site 9. In step 516, the location of the first dilator is observed with the assistance of the at least one locating element. In various embodiments, this observation can be performed concurrently with the advancement of the first dilator. In step 518, a stimulation lead is advanced through the body to the stimulation site 9. In some embodiments, the first dilator and guidewire are removed before advancing the stimulation lead in step 518. In some embodiments, all components are removed leaving only a stimulation lead after step 518.

Figure 8:
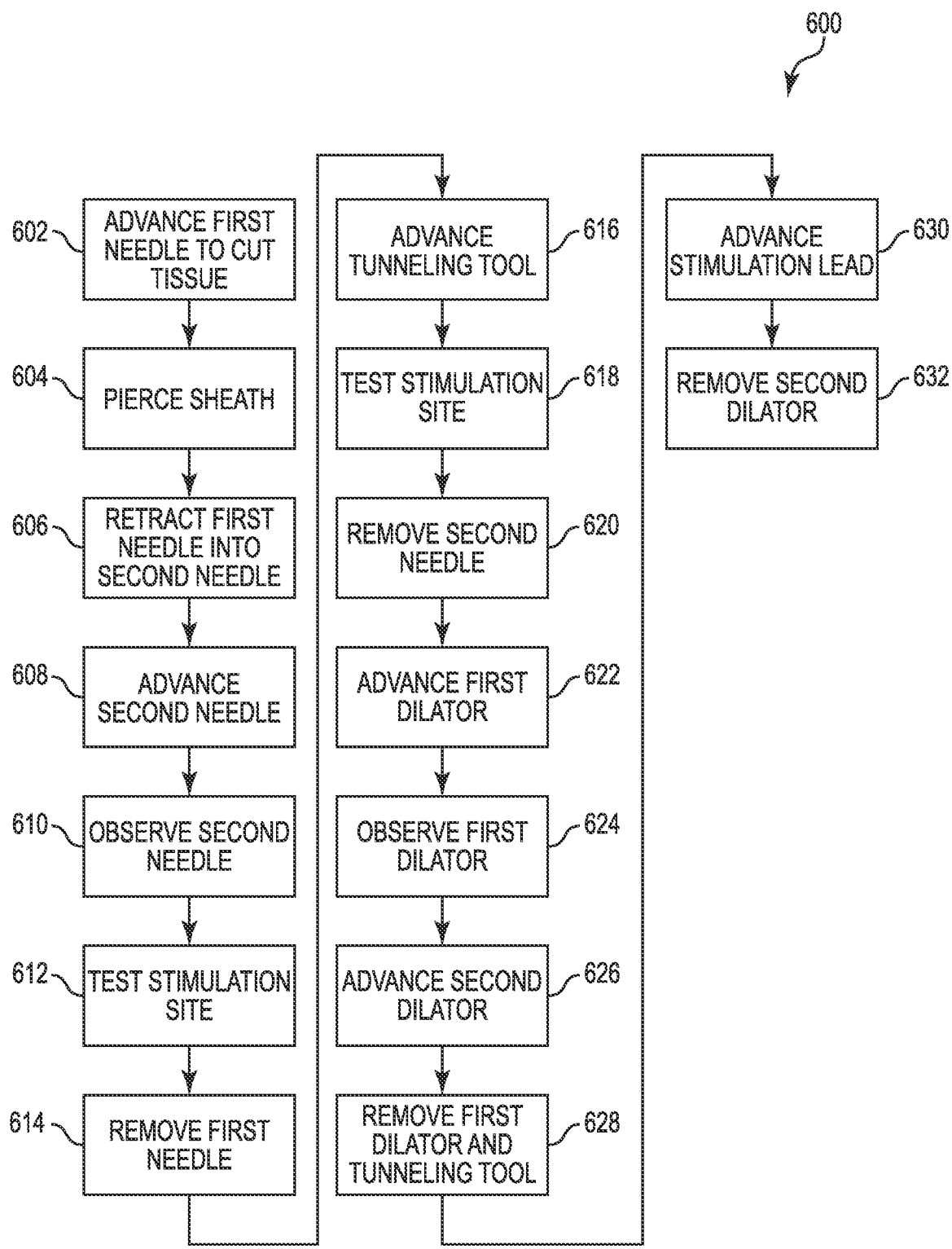
FIG. 8 is a detailed flow diagram of an exemplary method consistent with FIG. 7 for use with a lead system including a needle assembly and a dilator assembly, according to some embodiments.

FIG. 8 is a detailed flow diagram of an exemplary method 600 of using a lead delivery system consistent with FIG. 7, according to some embodiments. In some embodiments, method 600 is a method of using needle assembly 11 and dilator assembly 100. In step 602, a first needle is advanced through a body to cut through tissue, such as muscle tissue 8. In some embodiments, the first needle is protracted beyond a distal end of a second needle. In step 604, a sheath within the body is pierced, such as the carotid sheath 3, by the inner needle 14. In step 606, the first needle is retracted into the second needle to prevent it from cutting structures while inside the sheath. In some embodiments, the second needle has one or more locating elements and/or one or more imaging elements.

In step 608, the second needle is advanced in the sheath toward the stimulation site 9. In some embodiments, step 608 is omitted. In step 610, location of the second needle is observed using the one or more locating elements and/or one or more imaging elements. In various embodiments, this observation can be performed while advancing the second needle within the tissue. In some embodiments, step 610 is also performed prior to piercing the carotid sheath in step 606 to help determine the location of a second needle in relation to the carotid sheath using an imaging element. In step 612, the stimulation site 9 is electrically tested with the distal end of the second needle with an electrical signal delivered through the inner needle from a conductive wire (e.g., 46) extending outside the body to verify the stimulation site 9 near the vagus nerve 2.

In step 614, the first needle is removed. In step 616, a guidewire (i.e., tunneling tool) is advanced in the interior of the sheath to the stimulation site 9. The inner needle is not advanced through the interior of the carotid sheath 3. In step 618, the stimulation site 9 is electrically tested by the guidewire, specifically an electrode on the guidewire to verify the stimulation site 9 near the vagus nerve 2. In step 620, the second needle is removed.

In step 622, a first dilator having at least one locating element is advanced, in particular, through the interior of the sheath toward the stimulation site 9 to dilate a passage in the interior of the sheath. In some embodiments, advancing the first dilator expands the passage to have an effective diameter of about 4 French (4 F). In step 624, the first dilator is observed with the assistance of the at least one location element. Observation can be done concurrently with the advancement of the first dilator. In step 626, a second dilator is advanced within the sheath to further dilate the passage within the sheath. In some embodiments, advancing the second dilator expands the passage to about 6 French (6 F). In step 628, the first dilator and guidewire are removed, leaving the second dilator in place. In step 630, a stimulation lead is advanced through the body to the stimulation site 9. In step 632, the second dilator is removed. In some embodiments, removing the second dilator comprises splitting the second dilator and peeling it away from the guidewire.

Figure 9:
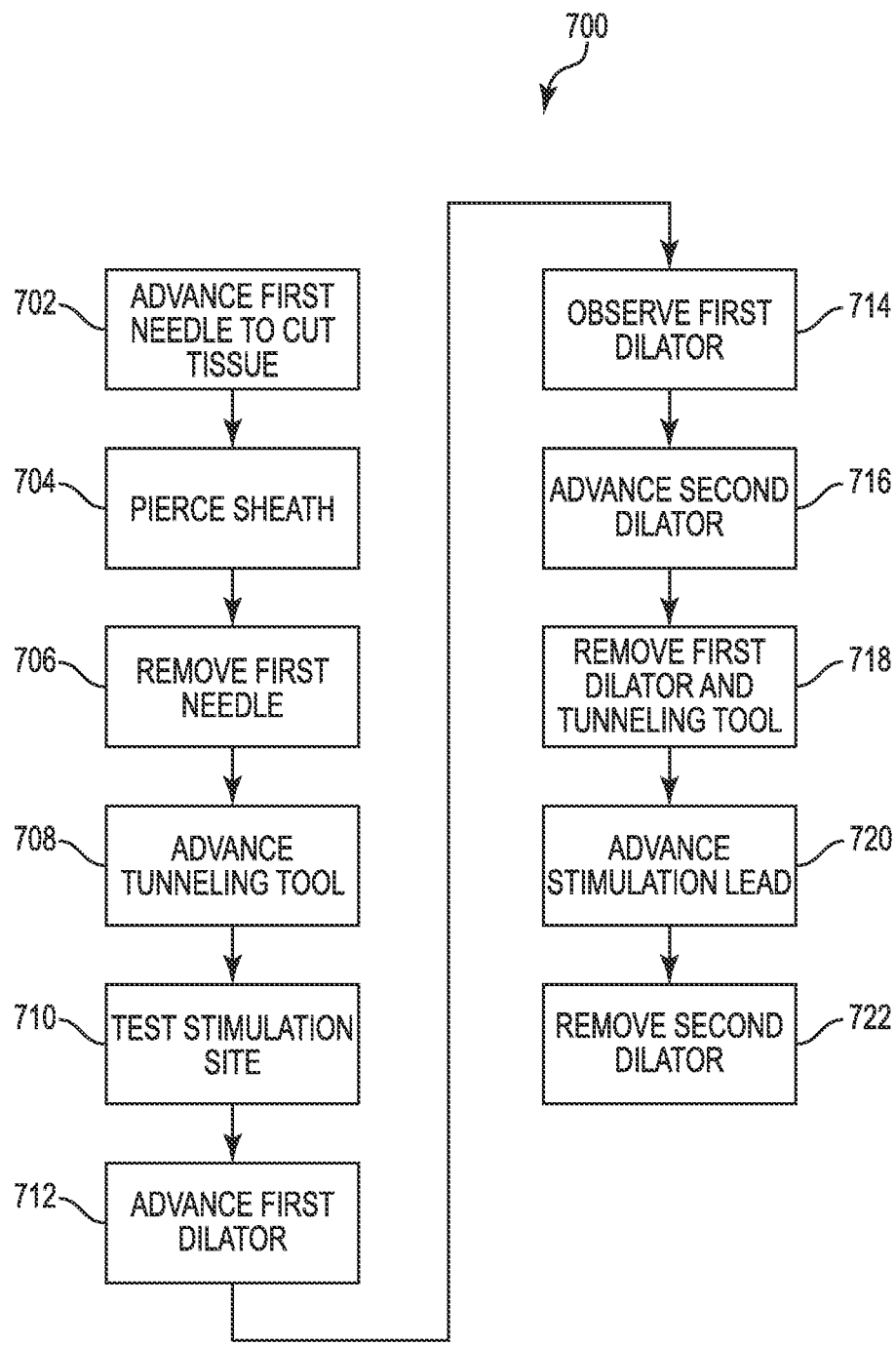
FIG. 9 is a detailed flow diagram of another exemplary method consistent with FIG. 7 for use with a lead system including a needle assembly and a dilator assembly, according to some embodiments.

FIG. 9 is a detailed flow diagram of another exemplary method 700 of using a lead delivery system consistent with FIG. 7, according to some embodiments. In some embodiments, method 700 is a method of using dilator assembly 302. In step 702, a first needle is advanced through a body to cut through tissue, such as muscle tissue 8. In some embodiments, the first needle is protracted beyond a distal end of a guidewire. In some embodiments, the first needle includes a locating element, such an echogenic element readily visible by ultrasound, and is a Tuohy needle. In step 604, a sheath within the body is pierced, such as the carotid sheath 3 by the first needle. In step 706, the first needle is removed to prevent it from cutting structures in the sheath.

In step 708, a guidewire (i.e., tunneling tool) is advanced in the interior of the sheath to the stimulation site 9. In step 710, the stimulation site 9 is electrically tested by the guidewire, specifically an electrode on the guidewire, to verify the stimulation site 9 near the vagus nerve 2. In step 712, a first dilator having at least one locating element is advanced, in particular, through the interior of the sheath toward the stimulation site 9 to dilate a passage in the interior of the sheath. In step 714, the location of the first dilator is observed with the assistance of the at least one location element. Observation can be done concurrently with the advancement of the first dilator.

In step 716, a second dilator is advanced within the sheath to further dilate the passage within the sheath. In step 718, the first dilator and guidewire are removed, leaving the second dilator in place. In step 720, a stimulation lead is advanced through the body to the stimulation site 9. In step 722, the second dilator is removed. In some embodiments, removing the second dilator comprises splitting the second dilator and peeling it away from the guidewire.

Figure 10:
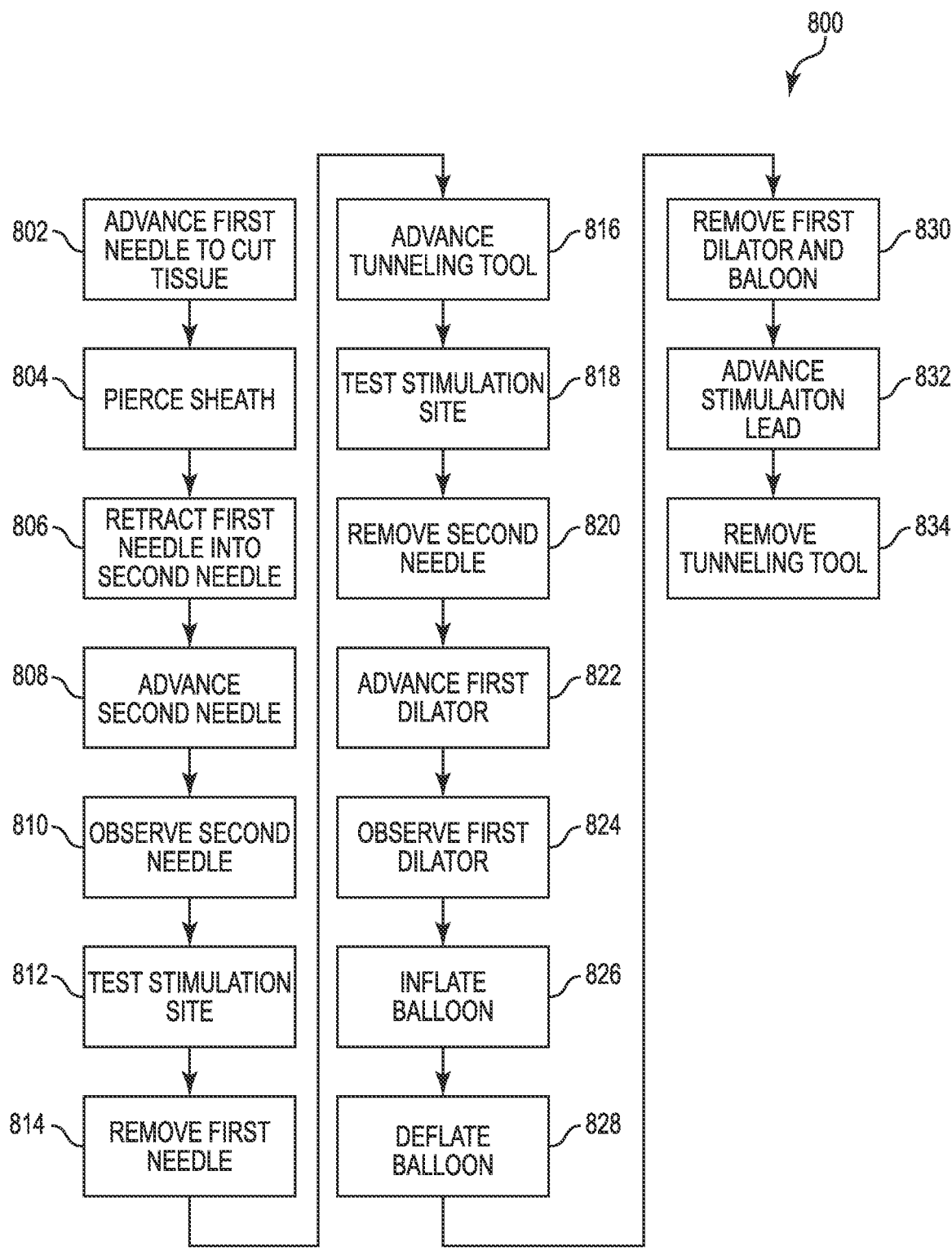
FIG. 10 is a detailed flow diagram of yet another exemplary method consistent with FIG. 7 for use with a lead delivery system including a balloon, according to some embodiments.

FIG. 10 is a detailed flow diagram of yet another exemplary method 800 of using a lead delivery system consistent with FIG. 7, according to some embodiments. Method 800 begins similarly to method 600, and steps 802, 804, 806, 808, 810, 812, 814, 816, 818, 820, 822, and 824 are similarly numbered as the similar steps of method 600. However, method 800 differs from method 600 beginning with step 826. In some embodiments, method 800 is a method of using needle assembly 11 and dilator assembly 202.

In step 826, an inflatable balloon is inflated on the first dilator. In some embodiments, the inflated balloon expands the passage to about 6 French (6 F). In step 828, the inflatable balloon is deflated. In step 830, the first dilator and inflatable balloon are removed from the body. In step 832, a stimulation lead is advanced through the body to the stimulation site 9 over the guidewire (i.e., tunneling tool). In step 834, the guidewire is removed.

Figure 11:
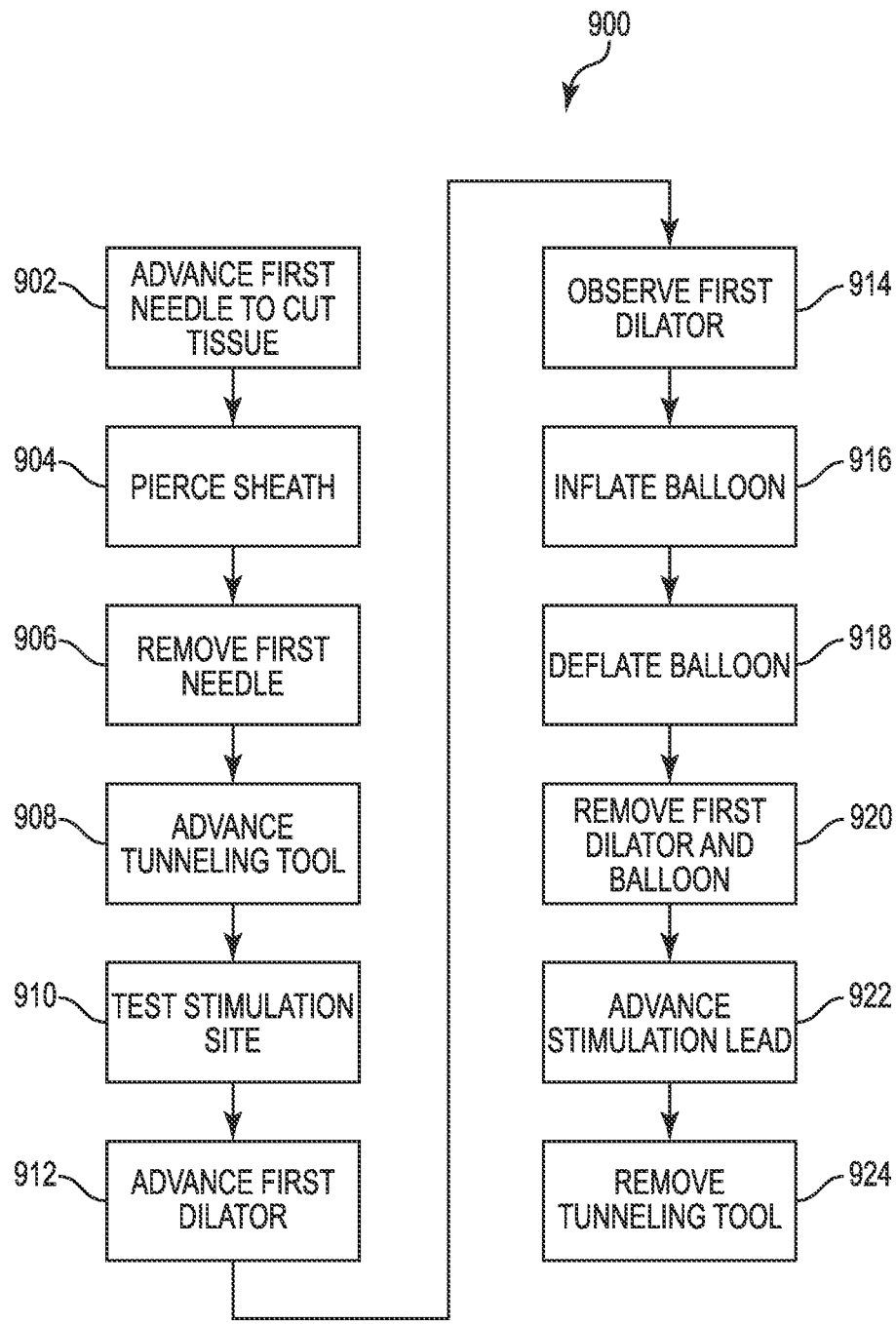
FIG. 11 is a detailed flow diagram of a further exemplary method consistent with FIG. 7 for use with a lead delivery system including a balloon, according to some embodiments.

FIG. 11 is a detailed flow diagram of a further exemplary method 900 of using a lead delivery system consistent with FIG. 7, according to some embodiments. In some embodiments, method 900 is a method of using dilator assembly 402. Method 900 begins similarly to method 700, and steps 902, 904, 906, 908, 910, 912, and 914 are similarly numbered as the similar steps of method 700. However, method 900 differs from method 700 beginning with step 916.

In step 916, an inflatable balloon is inflated on the first dilator. In some embodiments, the inflated balloon expands the passage to about 6 French (6 F). In step 918, the inflatable balloon is deflated. In step 920, the first dilator and inflatable balloon are removed from the body. In step 922, a stimulation lead is advanced through the body to the stimulation site 9 over the guidewire (i.e., tunneling tool). In step 924, the guidewire is removed.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. In some embodiments, the systems, methods, and apparatuses described for use with the vagus nerve can be used, or adapted to be used, with other neural targets, such as renal nerves, sympathetic ganglia, hypoglossal nerve, and the carotid sinus nerve. Accordingly, the scope of the present invention is intended to embrace all such alternatives, modifications, and variations as fall within the scope of the claims, together with all equivalents thereof.

We claim:

1. A method of introducing a stimulation lead into a body with a lead delivery system, the body having tissue and a sheath, the sheath having an interior and a stimulation site within the interior, comprising:

advancing a first needle through a distal end of a second needle such that the first needle is protruding from the distal end of the second needle;

cutting at least one of the tissue and the sheath with the first needle protruding from the second needle, such that the first needle advances subcutaneously through the tissue toward and into the sheath in the body;

retracting the first needle into the second needle, after advancing the first needle subcutaneously through the tissue and into the sheath, to prevent the first needle from cutting structures in the interior of the sheath;

advancing the second needle along the interior of the sheath to the stimulation site;

removing the first needle from the second needle;

advancing a guidewire through the second needle and along the interior of the sheath to the stimulation site after removing the first needle from the second needle;

testing the stimulation site, after advancing the guidewire through the second needle, using an electrode on at least one of the second needle and the guidewire, to verify that the stimulation site is adjacent a targeted nerve;

removing the second needle from the guide wire;

advancing a first dilator on the guidewire along the interior of the sheath toward the stimulation site to dilate a path in the interior of the sheath after removing the second needle from the guide wire; and observing the first dilator in the body using at least one of a locating element and an imaging element on the first dilator to facilitate at least one of locating and navigating the first dilator in the interior of the sheath.

2. The method of claim 1, further comprising:

observing the second needle in the body using at least one of a locating element and an imaging element on the second needle to facilitate at least one of locating the second needle and navigating the second needle to the stimulation site.

3. The method of claim 1, further comprising:

advancing a second dilator on the first dilator along the interior of the sheath toward the stimulation site;

removing the first dilator and the guidewire from the body;

advancing a stimulation lead to the stimulation site; and removing the second dilator.

4. The method of claim 1, further comprising:

inflating a dilating balloon on the first dilator;

deflating the dilating balloon;

removing the first dilator and dilating balloon from the body; and advancing a stimulation lead to the stimulation site.

5. The method of claim 1, further comprising:

advancing a second dilator on the first dilator along the interior of the sheath toward the stimulation site;

removing the first dilator and the guidewire from the body;

advancing a stimulation lead to the stimulation site; and splitting the second dilator for lateral removal.

6. The method of claim 1, further comprising:

inflating a dilating balloon on the first dilator;

deflating the dilating balloon;

removing the first dilator and inflatable balloon from the body;

advancing a stimulation lead to the stimulation site over the guidewire; and removing the guidewire from the body.

7. The method of claim 1, comprising testing the stimulation site by electrically stimulating the stimulation site through the first needle and a distal end of the second needle.

8. The method of claim 1, wherein testing the stimulation site comprises electrically stimulating the stimulation site through an electrode on a distal end of the guidewire.

9. A method of introducing a stimulation lead into a body with a lead delivery system, the body having tissue and a sheath, the sheath having an interior and a stimulation site within the interior, comprising:

advancing a needle on a guidewire that extends through a distal end of the needle until the needle is advanced past and extends past a distal end of the guidewire;

cutting at least one of the tissue and the sheath with the needle that extends past the distal end of the guidewire;

advancing the needle that extends past the distal end of the guidewire subcutaneously through tissue toward and into the sheath in the body;

removing the needle from the guidewire;

advancing the guidewire along the interior of the sheath to the stimulation site;

testing the stimulation site, at one or more times of before removing the needle from the guide wire and after removing the needle from the guidewire, using an electrode on the guidewire to verify that the guide wire at the stimulation site is adjacent a targeted nerve;

advancing a first dilator on the guidewire along the interior of the sheath toward the stimulation site to dilate a path in the interior of the sheath after testing the stimulation site; and observing the first dilator in the body using at least one of a locating element and an imaging element on the first dilator to facilitate at least one of locating and navigating the first dilator in the interior of the sheath.

10. The method of claim 9, further comprising:

advancing a second dilator on the first dilator along the interior of the sheath toward the stimulation site;

removing the first dilator and the guidewire from the body;

advancing a stimulation lead to the stimulation site; and removing the second dilator.

11. The method of claim 9, further comprising:

inflating a dilating balloon on the first dilator;

deflating the dilating balloon;

removing the first dilator and dilating balloon from the body; and advancing a stimulation lead to the stimulation site.

12. The method of claim 9, further comprising:

advancing a second dilator on the first dilator along the interior of the sheath toward the stimulation site;

removing the first dilator and the guidewire from the body;

advancing a stimulation lead to the stimulation site; and splitting the second dilator for lateral removal.

13. The method of claim 9, further comprising:

inflating a dilating balloon on the first dilator;

deflating the dilating balloon;

removing the first dilator and inflatable balloon from the body;

advancing a stimulation lead to the stimulation site over the guidewire; and removing the guidewire from the body.

\* \* \* \* \*